(12) United States Patent
Zamoyski

(10) Patent No.: US 6,559,178 B1
(45) Date of Patent: May 6, 2003

(54) COMPOSITIONS AND METHODS FOR APOPTOTIC CHEMOSURGERY

(76) Inventor: Mark Zamoyski, 988 Foothill Dr., San Jose, CA (US) 95123

( * ) Notice: Subject to any disclaimer, the term of this patent is extended or adjusted under 35 U.S.C. 154(b) by 0 days.

(21) Appl. No.: 10/059,653

(22) Filed: Jan. 29, 2002

(51) Int. Cl.$^7$ ............................................... A61K 31/35
(52) U.S. Cl. ....................... 514/453; 514/449; 514/451; 514/450
(58) Field of Search ................. 514/449, 451, 514/450, 453

(56) References Cited

U.S. PATENT DOCUMENTS

| | | | |
|---|---|---|---|
| 4,332,732 A | 6/1982 | Schmitz et al. | |
| 4,352,936 A | 10/1982 | Kaneko | |
| 4,744,981 A | 5/1988 | Pavanasasivam | |
| 4,906,452 A | 3/1990 | Sivam | |
| 5,981,568 A | * 11/1999 | Kunz et al. ................. | 514/411 |
| 6,342,520 B1 | 1/2002 | Zamoyski | |

FOREIGN PATENT DOCUMENTS

| | | | |
|---|---|---|---|
| WO | 99/40912 | * | 8/1999 |

OTHER PUBLICATIONS

Fauci et. al., Harrison's Principles of Internal Medicine, 14th edition, McGraw Hill, 1998, pp. 527–532.
Braunwald et. al., Harrison's Principles of Internal Medicine, 15th edition, McGraw Hill, 2001, p. 608.
Alberts et. al., Molecular Biology of the Cell, Third Edition, Garland Publishing 1994, pp. 89, 958–959, 1076, 1208.
U. S. Amriid, "Understanding the Threat", website printout on Aug. 27, 1999, 4 pages.
U. S. Amriid, "Trichothecene Mycotoxins (T–2)", website printout on Jan. 18, 1999, one page RE: toxicity by oral ingestion.
American Medical Association Encyclopedia of Medicine, Random House, 1989, p. 826, Retropubic Prostatectomy and Transurethral Prostatectomy.
Rubenstein et. al., "Transurethral Microwave Thermotherapy of the Prostate (TUMT)", eMedicine Journal, Jun. 29, 2001, vol. 2, No. 6 pp. 1–13.
Steinbecker et. al., "Transurethral Needle Ablation of the Prostate (TUNA)", eMedicine Journal, Jan. 10, 2002, vol. 3, No. 1 pp. 1–8.
Shelton et. al., "Tumescent Liposuction", eMedicine Journal, Dec. 5, 2000, vol. 1, No. 12 pp. 1–6.
Baxter et. al., "Liposuction, Techniques: Internal Ultrasound Assisted", eMedicine Journal, Oct. 22, 2001, vol. 2, No. 10 pp. 1–5.
Duke et. al., "Cell Suicide in Health and Disease", Mindspring .com, website printout on Jan. 19, 2002, 6 pages.
U. S. Amriid, "Understanding the Threat", website printout on Aug. 27, 1999, pp. 2–3 for LD50 of T–2 in humans.
Dearborn et. al., Morbidity and Mortality Weekly Report, Dec. 9, 1994, vol. 43, No. 48, pp. 881–883.
Okazaki et. al., "Antiviral Activity of Macrocyclic Trichothecene Mycotoxins . . . " Agricultural and Biological Chemistry, 1989, vol. 53 pp. 1441–1443.
Okazaki et. al., "Inhibition by Trichothecene Mycotoxins of Replication of Herpes Simplex Virus Type 2", Argicultural and Biological Chemistry, 1988, vol. 52 pp. 795 801.
Theodorescu et. al., "Prostate Cancer: Brachytherapy (Radioactive Seed Implantation Therapy)", eMedicine Journal, Oct. 19, 2001, vol. 2, No. 10, see pp. 10–11 for TRUS guidance procedures.

* cited by examiner

*Primary Examiner*—Dwayne C. Jones
*Assistant Examiner*—C. Delacroix-Muirheid

(57) ABSTRACT

Sesquiterpene epoxide compounds (trichothecenes) and methods for administering such compounds to achieve apoptotic ablation of internal organs or internal non-malignant cell populations are disclosed.

9 Claims, 2 Drawing Sheets

COMPOSITIONS AND METHODS FOR APOPTOTIC CHEMOSURGERY

BACKGROUND—SUMMARY

The current invention proposes interstitial administration of therapeutically effective doses of certain sesquiterpene epoxides (trichothecenes) to achieve ablation of non malignant cells in a selected organ or internal tissue mass.

BACKGROUND

Surgery remains the primary mode of ablation of non malignant tissue. The trend in prior art has been toward minimally invasive surgery through the use of various devices that can be inserted through small incisions or natural body orifices to reach and destroy the desired tissue. These devices employ a variety of means for ablation of tissue including cutting implements, devices for heating tissue, and devices for freezing of tissue. The destruction of tissue by these means results in cell death through necrosis.

Present invention departs from prior art in two significant respects. First, it provides a means of chemosurgery for ablation of tissue. Second, it provides a means of ablation that is accomplished by apoptosis versus prior art's necrosis. The advantages of apoptosis over necrosis will be discussed later in this application.

PRIOR ART TREATMENTS

Prior art ablation of internal tissues can broadly be divided into three categories; Conventional Surgery, Minimally Invasive Surgery, and Minimally Invasive Non Surgical Ablation.

Conventional Surgery involves making a significant incision through the skin and all underlying layers of tissue to reach a desired organ or tissue mass. All or portion of the organ or tissue mass is then cut and removed.

Minimally Invasive Surgery involves making a small incision or using an existing body orifice, insertion of a endoscope or laparoscope fitted with grasping and cutting tools or similar device, and ablation of a desired tissue mass by cutting.

Minimally Invasive Non Surgical Ablation involves insertion of devices other than grasping and cutting tools to destroy a target tissue mass.

Since applicant could not find any comparable prior art methods using chemosurgery for the more common procedures envisioned under present invention, the closest prior art comparable is Minimally Invasive Non Surgical Ablation. Consequently, a further discussion of prior art Non Surgical Ablation follows.

Non Surgical Ablation devices are generally tailored to the condition being treated or tissue mass targeted for ablation. Examples of prior art methods for treating two common conditions are presented below for illustrative purposes. Later, in the reduction to practice portion of this application, composition and methods for treating these conditions using apoptotic chemosurgery will be presented to contrast the novelty and utility of present invention's methods over prior art.

Benign Prostatic Hypertrophy (BPH)

An estimated 50% of men have histologic evidence of BPH by age 50, which increases to 75% in men older than 80 years of age. In 40–50% of these patients BPH becomes clinically significant. The prostate is a chestnut shaped body surrounding the beginning of the urethra in the male. The adult prostate weighs about 20 grams. In most men the prostate begins to enlarge further as they age. Prostatic enlargement compresses the urethra and may interfere with urination. BPH is characterized by an increased number of epithelial and stromal cells which may be the result of impaired programmed cell death (Steinbecker et. al. eMedicine Journal, Vol. 3, No. 1, Jan. 10, 2002).

Conventional surgery to remove all or part of the prostate is called a retropubic prostatectomy and involves making an incision in the abdomen and removal of prostatic tissue by hand and cauterization of bleeding vessels.

Minimally invasive surgery is called transurethral resection of the prostate (TURP). A resectoscope is passed up the urethra, a cutting edge or heated wire loop is then used to cut away as much of the prostatic tissue as possible, and a catheter is left in the urethra for several days as it heals.

Non surgical ablation methods employed under prior art include Transurethral Microwave Thermotherapy of the Prostate (TUMT), Transurethral Needle Ablation of the Prostate (TUNA), and Transurethral Laser Incision of the Prostate (TULIP).

TUMT involves insertion of a specially designed Foley-type catheter into the bladder allowing a microwave antenna to be properly positioned. TUMT uses microwaves in the 900–1100 kHz spectrum to create heat for the destruction of prostatic tissue (Rubenstein, "Transurethral Microwave Thermotherapy of the Prostate (TUMT)", eMedicine Journal, Vol. 2, No. 6, Jun. 29, 2001).

TUNA operates at 490 kHz and uses two needles deployed from the catheter tip as electrodes. As the prostate cells resist the passage of current between the two needle electrodes, heat is produced, resulting in necrosis of the tissue (Steinbecker, "Transurethral Needle Ablation of the Prostate (TUNA)", eMedicine Journal, Vol. 3, No. 1, Jan. 10, 2002).

TULIP is also mentioned in prior art. TULIP employs a laser. Lasers heat tissue, once again inducing necrotic cell death.

Under present invention, therapeutically effective amounts of trichothecene would be injected into the prostate to achieve a desired amount of ablation. Since compositions of present invention induce apoptosis, they would be much less traumatic than the necrotic methods employed under prior art.

Liposuction

Liposuction is the most commonly performed cosmetic procedure in the US.

Traditional liposuction involves insertion of a cannula through an incision. The cannula is a hollow tube with one or more openings for breaking down tissue and a vacuum is provided for aspiration. The cannula is moved back and forth repeatedly to rasp off and aspirate fat cells.

Internal Ultrasound Assisted Liposuction uses a cannula capable of emitting mechanical vibration energy greater than 16 kHz to enhance fat removal. The goal of using ultrasound is to achieve emulsification by microcavitation. Alternating compression and expansion cycles create microbubbles during the expansion cycle and as the bubble collapses during the compression cycle core temperatures may momentarily reach 72,000 Kelvin or higher resulting in a pulse of electromagnetic radiation termed sonoluminescence. Although Ultrasound Assisted Liposuction has the potential for less connective tissue damage than conventional liposuction, it requires continuous infusion of a wetting solution to conduct the sound waves. Additionally, short term complications include high rates of seromas and skin burn and long term issues involve concerns about DNA damage (part of the sonoluminescence is in the soft X-Ray range) and sonochemical effects such as disruption of chemical bonds resulting in the formation of free radicals and other reactive ions (Baxter, "Liposuction Techniques: Internal Ultrasound Assisted", eMedicine Journal, Vol. 2, No. 10, Oct. 22, 2001)

Under present invention, therapeutically effective amounts of trichothecene would be injected into a given area to achieve a desired amount of ablation. Since compositions of present invention induce apoptosis, they would be much less traumatic than the necrotic methods employed under prior art. Present invention would also not harm any connective tissue as compositions of present invention function only on nucleated cells.

Because present invention operates by apoptosis versus prior art's necrosis a brief discussion of both is presented to demonstrate the significant utility of present invention's method of cell death over prior art's method of cell death.

Apoptosis Versus Necrosis

Necrotic death occurs when a cell is injured by oxygen deprivation or by a physical assault such as that from surgical procedures. Swelling and inflammation are hallmarks of necrosis. Directly damaged cells that are ruptured spill their contents into the surrounding area. Partially damaged cells that are no longer able to control their fluid and ion balance swell and rupture as charged particles such as sodium and calcium ions that are normally pumped out, now stream in. Inflammation begins as macrophages and other white blood cells of the immune system converge on the necrotic cells. The activation of an immune response to the injury initiates numerous events that range from secretions of the white cells that cause further damage to normal tissue in the vicinity of the injury to the production of growth and other factors to facilitate regrowth as part of an "injury response".

A cell undergoing apoptosis sees very different changes. There is no swelling and no inflammatory response. Instead the dying cell shrinks and pulls away from its neighbors. Some of these shrunken apoptotic cells are ingested by neighboring cells. Dying cells that are not consumed may undergo further changes dividing into a number of "apoptotic bodies" that are removed quietly (Duke et. al., "Cell Suicide in Health and Disease" per IDS).

Protein Synthesis Inhibition

The compositions proposed under present invention are protein synthesis inhibitors (PSIs). Accordingly a brief background about protein synthesis and cellular function is presented.

The most fundamental function a cell is protein synthesis (i.e. expression of its DNA). Proteins make up ~60% of a dry cell's mass by weight. In very broad and general terms, as cells mature and differentiate in the body, they reach an equilibrium in protein synthesis and protein degradation and settle down to perform their given function in this relative state of homeostasis. There are two notable exceptions that cause massive perturbations to this homeostasis: 1) when a cell is called upon to grow and divide and 2) when certain secretory cells are called upon to produce large amounts of proteins for secretion. Although the cell signaling signaling pathways, intracellular transduction pathways, and spectrum of protein(s) to be produced are quite different in growth versus secretion, normal growth and secretion events share one major similarity in their end result: massively accelerated protein synthesis. A cell that is called on to grow (cycling cell) has as much as 5 times the protein synthesis activity of a non cycling cell and needs between 2,000 and 5,000 different enzymes and structural proteins to grow and divide. Likewise, secretory cells such as those of the immune system become protein factories producing massive amounts of antibodies, mediators, growth factors, or other proteins when stimulated to do so.

There are also abnormal conditions such as cancer and viral infections that share the same property of hyperactive protein synthesis versus normal quiescent cells. Viruses invade a cell, parasitize the host cellular machinery, and convert the cell into a factory producing massive amounts of viral proteins, much like a secretory cell. Cancer is a growth and divide type event, and even though the signaling mechanism is different in that it is self-induced intracellularly by several genetic mutations, the end result is also hyperaccelerated protein synthesis characteristic of a cycling cell.

Inhibiting protein synthesis effects cells in a dose dependent manner and effects actively cycling cells differently than non cycling cells. At low doses, protein synthesis inhibitors (PSIs) stop actively cycling cells from cycling without killing them (hereinafter referred to as inhibitory or G zero inducing dose). Inhibitory doses also stop hyperaccelerated protein synthesis by secretory cells. At moderate doses PSIs exhibit toxicity to actively cycling cells (hereinafter referred to as the cytotoxic dose). At high doses, PSIs exhibit toxicity to all cells (hereinafter referred to as the toxic dose).

NOVELTY AND UNOBVIOUSNESS OVER PRIOR ART

Novelty and Unobviousness

First, present invention takes the novel approach by using chemosurgery for ablation of tissue versus prior art's mechanical devices.

Second, present invention takes a novel approach of inducing apoptosis versus prior art's methods of inducing necrosis.

Third, present invention also employs novel administration methods and dose levels of trichothecenes versus any of prior art's uses of trichothecenes. Prior art has attempted using cytotoxic dose levels of trichothecene against hyperproliferative conditions such as cancer, however they have failed. Anguidine, a simple trichothecene, was tested against cancer and abandoned after Phase II testing showed a low tumor response and considerable hematologic toxicity. Prior art attempts to remedy this failure are embodied in U.S. Pat. Nos. 4,906,452 and 4,744,981 which propose conjugates of trichothecene with monoclonal antibodies to enhance delivery to the tumor and glycosylation of trichothecene to increase blood solubility. Present invention takes a novel and unobvious approach that is exactly opposite to prior art in several respects. First, present invention reverses direction of administration (i.e. administered from tissue side to blood versus prior arts direction of blood to tissue). Second, present invention embraces the non specific internalization properties to deliver the greatest doses to tissues it is applied to and depending on those tissues to retain the trichothecene, preventing the trichothecene from reaching general circulation (versus prior arts targeted delivery by monoclonal antibodies). Third, present invention embraces blood insolubility to prevent entry into the blood (versus prior art glycosylation). Fourth, present invention embraces the use of macrocyclic trichothecene (versus simple trichothecenes in prior art) because of enhanced localization attributes and narrower dose spectrum of biological effect (discussed later). Fifth, present invention administers toxic dose levels to target cell populations versus prior art's cytotoxic dose levels.

Utility Over Prior Art

There are several distinct advantages to using apoptotic chemosurgery versus prior art's mechanical devices and necrotic ablation methods.

First, apoptosis is a much cleaner method of cell death that does not result in swelling, inflammation, or an "injury response". Swelling and inflammation result in pain as nerves are compressed, and as such apoptotic chemosurgery provides a much less painful alternative to necrotic surgery. "Injury response" contributes to a cellularly "messy" healing with potential overproduction of connective tissue, which would also be obviated by apoptotic chemosurgery.

Second, apoptotic chemosurgery does not cause any connective tissue damage as only nucleated cells are subject to death. Mechanical devices that cut or heat cause indiscriminate damage to all tissue.

Third, apoptotic chemosurgery does not cause the large scale damage to blood vessels that mechanical cutting, heating, grasping, or rasping devices do.

The combination of the above factors will provide for reduced procedure times, little or no hospital stay required, faster recovery times, and greater probability of long term therapeutic benefit being maintained versus prior art's mechanical, necrotic, ablation methods.

SUMMARY OF THE INVENTION

Present invention proposes ablation of non malignant tissue cell populations by interstitial administration of therapeutically effective amounts of trichothecene.

BRIEF DESCRIPTION OF THE DRAWINGS

FIG. 1A shows the hyperactive protein synthesis inhibiting dose profile and nontoxic range in human cells of Roridin A, a representative macrocyclic trichothecene.

FIG. 1B shows the hyperactive protein synthesis inhibiting dose profile and nontoxic range in human cells of Satratoxin G, a representative macrocyclic trichothecene.

FIG. 2A shows the hyperactive protein synthesis inhibiting dose profile and nontoxic range in human cells of T-2, a representative simple trichothecene.

FIG. 2B shows the hyperactive protein synthesis inhibiting dose profile and nontoxic range in human cells of DAS, a representative simple trichothecene.

DETAILED DESCRIPTION OF THE INVENTION

The treatments disclosed below involve interstitial administration of biologically active trichothecenes to effectuate the cell death of targeted cell populations. Materials and methods for achieving this are described below.

Trichothecenes Defined

Fungi of the genera Fusarium, Myrotecium, Trichoderma, Stachybotrys and others produce Trichothecene mycotoxins. Trichothecenes constitute a family of fungal sesquiterpene epoxides that inhibit protein synthesis. Trichothecene mycotoxins are low molecular weight (250–700 daltons), non volatile compounds, and of over 150 trichothecenes have been identified. There are two broad classes: those that have only a central sesquiterpenoid structure and those that have an additional macrocyclic ring (simple and macrocyclic trichothecenes, respectively).

As used in this application, "therapeutics", "biologically active agent", or "trichothecene" are defined as either simple or macrocyclic trichothecenes and include molecules of the following general chemical formulas: Simple trichothecenes are categorized into three groups with the following chemical formulas:

Group A:

Where $R_1$ is H, OH, or $O-\overset{O}{\overset{\|}{C}}-CH_3$;

$R_2$ is H, OH, or $O-\overset{O}{\overset{\|}{C}}-CH_3$;

$R_3$ is H, OH, or $O-\overset{O}{\overset{\|}{C}}-CH_3$;

$R_4$ is H, or OH; and $R_5$ is H, OH, $O-\overset{O}{\overset{\|}{C}}-CH_3$ or $\overset{O}{\overset{\|}{C}}-O-CH_2(CH_3)_2$.

Group B:

Where $R_1$ is H, OH, or $O-\overset{O}{\overset{\|}{C}}-CH_3$;

$R_2$ is H, OH, $O-\overset{O}{\overset{\|}{C}}-CH_3$ or $O-\overset{O}{\overset{\|}{C}}-CH=CH-CH_3$;

$R_3$ is H, OH, or $O-\overset{O}{\overset{\|}{C}}-CH_3$;

$R_4$ is H, OH, or $O-\overset{O}{\overset{\|}{C}}-CH_3$;

Group C:

Where $R'$ is OH or $O-\overset{O}{\overset{\|}{C}}-CH=CH-CH_3$.

Macrocyclic Trichothecenes can be described by the following general chemical formulas:

[Chemical structure diagram]

Wherein $R_1$ is OH, or $OC(=O)-CH_3$;

$R_2$ is H, OH, $O-C(=O)-CH_3$ or $OCOCH_2CH(CH_3)_2$; and

R' is any molecule composed predominantly, or in its entirety, of combinations of C, H, and O:

Some representative examples of R' include:

Satratoxin H:

[Chemical structure: —CH= ring with OH, CH(CH₃)OH, CH=CHCH=CH—]

Satratoxin G:

[Chemical structure: —HC— epoxide ring with OH, CH(CH₃)OH, CH=CHCH=CH—]

or molecules of the following general formula:

[Chemical structure diagram]

Wherein $R_1$ is H, OH, or $O-C(=O)-CH_3$;

$R_2$ is H, OH, $O-C(=O)-CH_3$ or $OCOCH_2CH(CH_3)_2$; and

R' is any molecule composed predominantly, or in its entirety, of combinations of C, H, and O.

A more comprehensive listing of trichothecenes is included in U.S. Pat. Nos. 4,744,981 and 4,906,452, incorporated herein by reference.

Trichothecenes are fast acting potent inhibitors of protein synthesis in eucaryotic cells. Their main effects are on rapidly proliferating tissues such as bone marrow, skin, mucosa epithelia, and germ cells. The sesquiterpenoid ring binds to ribosomes, inhibiting protein synthesis. The macrocyclic ring enhances cell binding and internalization.

Trichothecenes are invisible to the immune system since they neither contain nor produce amino acids. Since trichothecene molecules contain only carbon, hydrogen, and oxygen they are not subject to proteolytic degradation. U.S. Pat. No. 4,906,452 (column 11 first paragraph) further discloses that some studies of the rates at which certain trichothecenes are converted into biologically inactive molecules (apotrichothecenes) found that macrocyclic trichothecenes are inactivated quite slowly and only by intracellular acid catalysis as might occur in lyzosomes.

Trichothecenes are extremely stable to heat and ultraviolet light inactivation. Heating to 500° F. for 30 minutes is required for inactivation. Brief exposure to NaOH destroys toxic activity. These substances are relatively insoluble in water but are highly soluble in ethanol, methanol, propylene glycol, and dimethyl sulfoxide.

Reduction to Practice—Selection of Trichothecenes for Use

Macrocyclic trichothecenes are preferred for use in present invention because they are relatively insoluble in blood and because the macrocyclic ring enhances cellular binding and internalization which tends to localize them more quickly and prevent their entry into general circulation.

An excellent in vivo example of this is the Cleveland Infant Model. The Cleveland infant model showed the reluctance of macrocyclic trichothecenes to enter the blood stream, and instead their tendency to localize into the epithelium with which they initially came into contact with.

The Cleveland Infant Model: The cluster of infant hemosiderosis in Cleveland (see Dearborn et. al., Morbidity and Mortality Weekly Report, Dec. 9, 1994, Vol. 43, No. 48, Pages 881–883) demonstrated, in vivo, in humans, the ability of certain macrocyclic trichothecenes to localize in tissue without appreciably entering general circulation. Adults and infants were subjected (inadvertently) to airborne (cytotoxic) concentrations of trichothecenes produced naturally by the fungus *Stachybotrys atra*. Trichothecenes produced by *S. Atra* include satratoxins H, G, F, roridin E, verrucarin J, and trichoverrols A and B.

The mean age of the infants was ~10 weeks old (range 4–16 weeks). At this age, the lungs of infants are growing at an accelerated rate, and the destruction of lung tissue clearly indicated cytotoxic airborne concentrations. In the infants examined, despite the acute pulmonary hemorrhage/hemosiderosis, the inhaled trichothecenes localized in the lung epithelium and did not enter circulation where they would have caused systemic cytotoxicity. Laboratory findings on admission showed a normal white blood cell count (median=13.8 cells/cubic mm) in the infants. Red blood cell counts were consistent with the blood loss from the hemosiderosis. No other source of bleeding (i.e. gastrointestinal or nasopharyngeal) was identified during endoscopic evaluation. This demonstrates both the reluctance of these macrocyclic trichothecenes to enter the blood stream as well as the tendency for them to localize into the epithelium with which they first came into contact with.

The likely molecular basis for the "localization" of these trichothecenes is their ability to be rapidly internalized into cells because of their macrocyclic ring combined with their insolubility in blood, which would tend to keep them out of the circulatory system. The incredibly small size of trichothecenes (~1 nm or less) allows them to travel between cells (~2–4 nm spacing). Once internalized they can travel through gap junctions. Gap junctions allow molecules smaller than 1000 daltons (~1.5 nm in diameter) to pass between connected cells and trichothecenes are comfortably under the size limitation at 250–700 daltons. Gap junction travel would tend to further localized trichothecenes within the organ or other gap junction connected tissue mass.

It is likely the inhaled trichothecenes were somewhat "trapped" between the lumen of the lungs on one side and the circulatory system on the other side, in which they are insoluble. In between this is the lung tissue in which they eventually internalized—in virtually the same way they would be expected to act when applied interstitially into an organ or tissue mass—internalizing in the organ or tissue mass without appreciably entering general circulation.

Figures 1A, 1B:
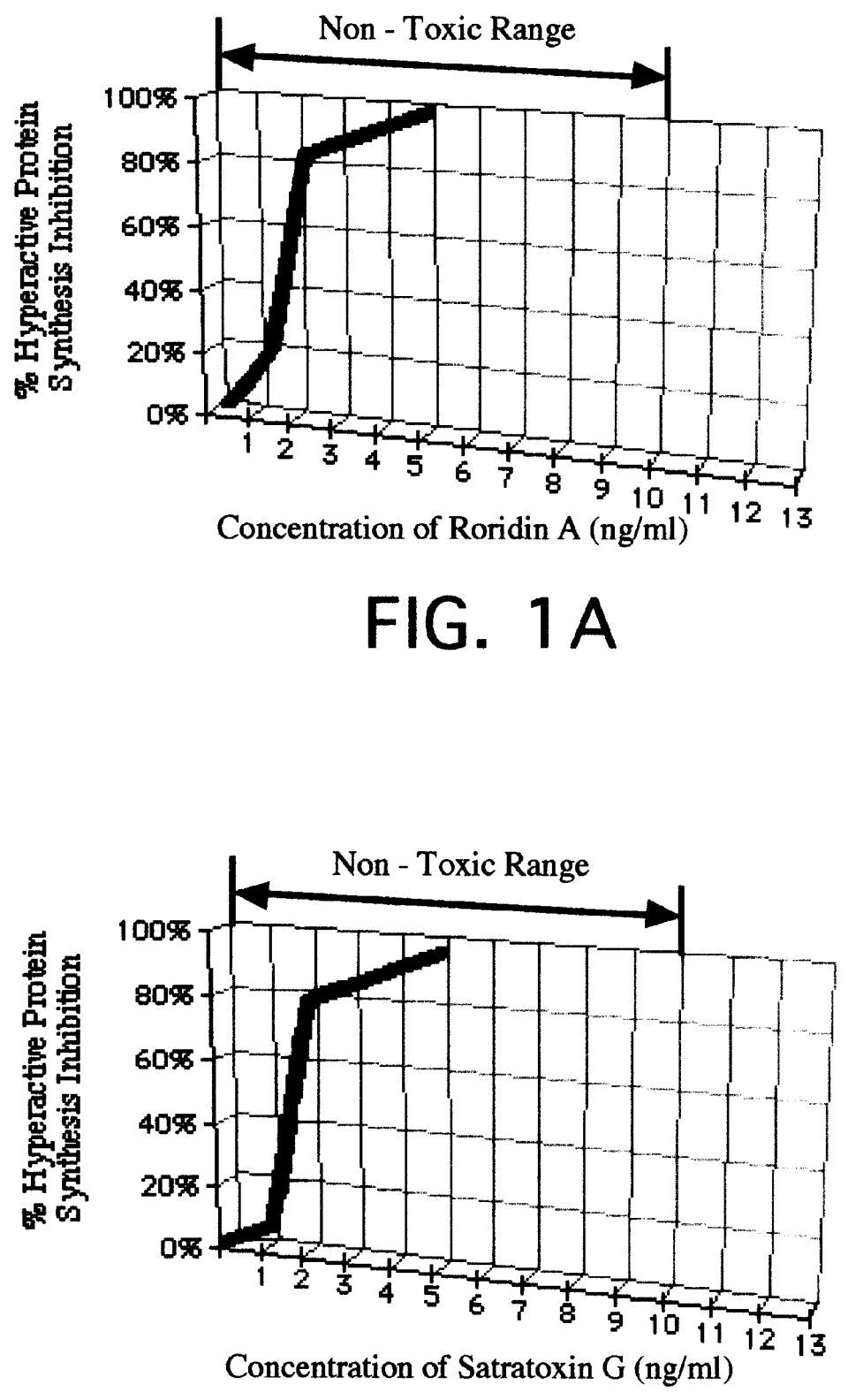
Figures 2A, 2B:
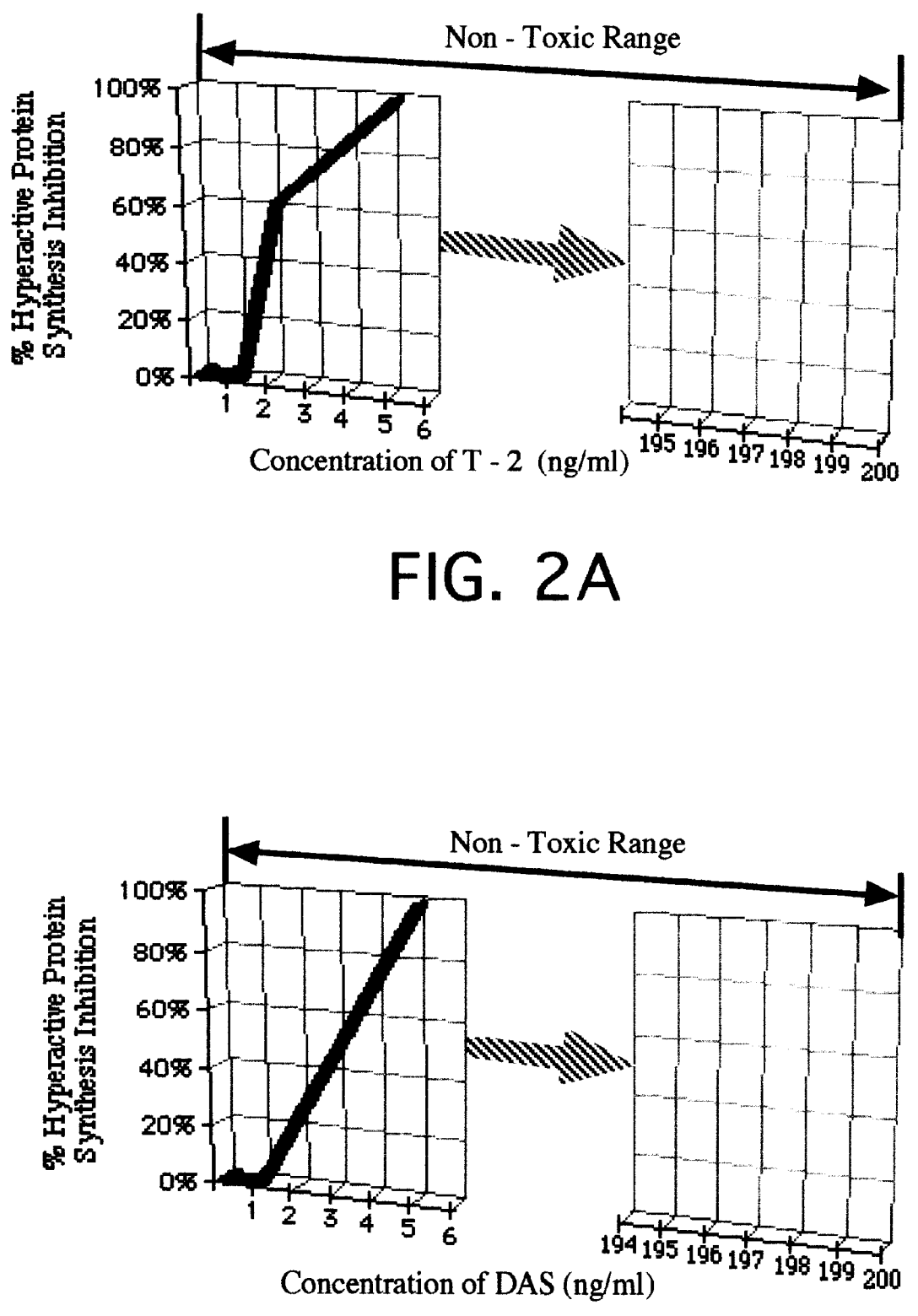

The other important aspect of macrocyclic trichothecenes is the spectrum of biological affect from inhibitory to cytotoxic to toxic is housed within a very narrow concentration range. FIGS. 1A and 1B show the protein synthesis inhibiting profiles of two macrocyclic trichothecenes and FIGS. 2A and 2B show the same for two representative simple trichothecenes. The narrow nontoxic range of the macrocyclics provide the ability to arbitrage the volume disparities between a selected tissue mass versus systemic circulation to provide a high margin of safety against systemic effects. This is discussed in more detail in the reduction to practice section under dose determination.

Reduction to Practice—Preparation of Trichothecenes

Fungi can be grown in culture and the trichothecenes extracted by centrifugal partition chromatography as described in Okazaki et al. or Tani et. al. and described in other literature such as Onji et. al. (Onji, Y., Aoki, Y., Yamazoe, Y., Dohi, Y., and Moriyamam, T., 1988 *Isolation of nivalenol and fusarenon-X from pressed barley culture by centrifugal partition chromatography, Journal Liquid Chromatography*, 11:2537–2546) or Jarvis et al. (Jarvis, B. B., R. M. Eppley, and E. P. Mazzola, 1983 *Chemistry and Bioproduction of the Macrocyclic Trichothecenes*, p 20–38. In Y. Ueno, *Trichothecenes: chemical, biological, and toxicological aspects*, vol 4. Elsevier Science Publishing Inc., New York) or Sorensen et al. (Sorenson, W. G., Frazer, D. G., Jarvis, B. B., Simpson, J., and Robinson, V. A., *Trichothecene Mycotoxins in Aerosolized Conidia of Stachybotrys atra*, June 1987 *Applied and Environmental Microbiology*, Vol. 53 No. 6, p. 1370–1375) where *S. atra* was grown on sterile rice, autoclaved, dried, and then aerosolized by acoustic vibration and collected on glass-fiber filters and extracted with 90% aqueous methanol.

Alternatively, certain trichothecene mycotoxins can be purchased from companies such as Sigma Chemical Co. St. Louis Mo., USA or Wako Pure Chemical Industries, Ltd., Japan, or Wellcome Research Labs, Buckinghamshire, England or Boehringer-Mannheim, Manheim, West Germany.

Reduction to Practice—Method of Administration

Preferred embodiment of current invention administers trichothecenes by hypodermic injection, mixed with a suitable carrier such as ethanol or propylene glycol. The latter serve no biological role other than to act a vehicle to facilitate uniform distribution of the trichothecene within an organ or tissue mass. These mixtures are hereinafter referred to as "therapeutic compositions" or "pharmaceutical compositions" or "compositions" and nothing in this application is intended to limit trichothecene from being mixed with any suitable substance that may facilitate administration, uniformity of distribution, enhance absorption, increase efficacy, or with other trichothecenes or any other substances that serve any other beneficial purpose, the aforementioned combinations also called "therapeutic composition" or "pharmaceutical compositions" of present invention. The term "therapeutics" or "therapeutics of present invention" is generally intended to refer to the biologically active trichothecene(s). Although preferred embodiment uses hypodermic needles any other devices or methods capable of interstitially delivering therapeutic compositions of present invention may be substituted.

Reduction to Practice—Dose Determination

The hyperactive protein synthesis inhibiting profiles were constructed from data collected from in vitro experiments using human epidermoid cells, virally infected with HSV-2 to induce a hyperactive state of protein synthesis, and conducted and reported by Okazaki et. al. in the attached Journal of Agricultural and Biological Chemistry articles. Since the Okazaki experiments were to determine viral inhibition properties, the data has been reformatted for relevance to present invention in establishing baseline "safe" levels. Stated data points were taken from Okazaki's text, other data points were read from the graph, the rest were computed by linear interpolation between the aforementioned data points. FIGS. 1A and 1B show the hyperactive protein synthesis inhibiting dose profile of roridin A and satratoxin G, respectively. Both roridin A and satratoxin G are macrocyclic trichothecenes. By ~5 ng/ml both had inhibited ~99% of the hyperactive protein synthesis. Both did not reduce cell viability at concentrations of 10 ng/ml or less. Toxicity started at concentrations greater than 10 ng/ml, and concentrations above 10 ng/ml are hereinafter referred to as Toxic Concentrations. Concentrations below 10 ng/ml are hereinafter referred to as Non Toxic and since at around 1 ng/ml almost no protein synthesis inhibition was observed (especially for Satratoxin) the 1 ng/ml level is hereinafter referred to as the "ultra safe level".

Determination of concentrations for use to achieve a desired level of ablation would be determined by subjecting the relevant cell type targeted for ablation to various concentrations of the selected trichothecene in vitro and determining the percent of cells that remain viable. Human cell lines are commercially available from several sources including ATCC—American Type Culture Collection, Manassas, Va., USA or ECACC—European Collection of Cell Cultures, Salisbury, Wiltshire, UK or DSMZ—German Collection of Microorganisms & Cell Cultures, Braunschweig, Germany or IZSBS—Istituto Zooprofilattico Sperimentale, Brescia, Italy or ICLC—Interlab Cell Line Collection, Genova, Italy or ECBR—European Collection for Biomedical Research, Genova, Italy or any other suitable supplier. The cell lines would be grown in culture and exposed to the trichothecene by methods described in Okazaki et al. or Tani et al. where human cell lines were grown in Eagle's minimum essential medium (MEM) supplemented with 10% fetal calf serum (FCS). Trichothecenes were then dissolved in dimethyl sulfoxide at a concentration of 20 mg/ml and diluted in Eagle's MEM. Stock solutions (200 $\mu$g/ml) were prepared, passed through a 450 -nm Millipore membrane filter and stored at −20° C. until use. Tissue culture plates would be seeded with a panel of human cell lines which would be allowed to proliferate at 37° C. until confluent monolayers had formed. Different culture plates would then be exposed to different toxic concentrations of the macrocyclic trichothecene (e.g. ~15 ng/ml, 20 ng/ml, etc . . . ), the resulting cell mortality in the various culture dishes would then be measured by trypan blue exclusion after trypsinization, and a profile of the percentage of cell mortality corresponding to a given concentration of the macrocyclic trichothecene would then be constructed. As an example, if 20 ng/ml resulted in the death of 50% of the cells in culture, this would be termed the 50% ablative concentration.

The selected concentration would then be converted to an administrable dose by simple mathematical methods. As an example, if we have a BPH patient with a prostate that is ~50 ml in mass and we would like to reduce it by ~50% (or 25 ml) to get it back closer to a normal size, the 50% ablative concentration of 20 ng/ml would translate into a 1000 ng total dose to be administered interstitially into the prostate (i.e. 50 ml.×20 ng/ml=1000 ng).

Reduction to Practice—Safety

The safety of the above example can be evaluated under a worst case scenario. The 50 ml prostate described above is a fairly small mass compared to the roughly 5.5 liters of blood or 42 liters of extracellular water outside the vascularization. Conservatively using the smaller volume of 5.5 liters of blood, our 1000 ng dose above, and assuming a worst case scenario where the entire 1000 ng dose is accidentally injected directly into the blood stream, there would be no health risk to the patient. Since the blood circulates roughly once per minute when a person is in a resting state, the 1000 ng dose would be almost instantly mixed in with the 5.5 liters of blood (i.e. 5500 ml) for a resulting blood concentration of 0.18 ng/ml (i.e. 1000 ng.÷5500 ml=0.18 ng/ml) which is less than one fifth of the 1 ng/ml concentration previously determined as "ultra safe".

Conversely, we can work in reverse to determine the worst case dose that may be injected directly into the blood and still be in the "ultra safe zone". That would be 5500 ng (i.e. 1 ng/ml×5500 ml of blood=5500 ng). Even a five times larger dose (5 ng/ml or 27,500 ng.) of satratoxin injected directly into the blood would not be toxic to the patient, but would only temporarily induce a G-zero or non cycling state in some of the bone marrow cells, a state from which they would emerge unharmed roughly 8 hours after intracellular inactivation of the trichothecene. The 5 ng/ml blood dose (i.e. 27,500 ng) is 50% of the nontoxic level of 10 ng/ml and is hereinafter referred to as the "safe dose" or "save dose level". Since present invention deals with interstitial administration, the rapid cellular internalization of the therapeutics and blood insolubility of the therapeutics would result in a practical "safe dose" level many times greater than the "safe dose" level presented under the worst case scenarios where it is injected directly into the blood. As an example, AMRIID computed T-2's LD50 (lethal dose to 50% of people) when administered by inhalation (crossing lung tissue to enter circulation) as 1.21 mg/kg of body weight. This translates into a 84,700,000 ng dose for the average 70 kg person to have a 50% chance of mortality. By contrast the 5500 ng "ultra safe" and 27,500 ng "safe" doses are 15,400 and 3,080 times smaller than the LD50, respectively.

Reduction to Practice—Administration Examples

Administration methods will vary depending on the organ or tissue mass targeted for ablation. Some examples are provided for clarification.

EXAMPLE 1A

An elderly patient presents with BPH and has difficulty urinating. The prostate is enlarged to roughly twice its normal size. The decision is made to use the 50% ablative dose (as computed above) to restore the prostate to a relatively normal size and relieve pressure on the urethra from the enlarged prostate.

In the preferred embodiment of present invention satratoxin is mixed with propylene glycol and administered by a plurality of hypodermic injections into the prostate, facilitated by the use of a transrectal ultrasound imaging device (TRUS) with template guidance, however any other suitable trichothecene or combination of trichothecenes, any other suitable carrier, or any other suitable means of administration may be substituted.

TRUS guidance was initially developed for implantation of radioactive seeds in the prostate for treatment of prostate cancer (see Theodorescu, "Prostate Cancer: Brachytherapy (Radioactive Seed Implantation Therapy" eMedicine Journal, Vol. 2, No. 10, Oct. 19, 2001, pages 8–11, incorporated herein by reference). Present invention substitutes the use of needles used to implant the radioactive seeds with hypodermic needles capable of injecting the trichothecene into the prostate instead. Image assisted guidance not only provides for more uniform distribution but allows avoidance of structures such as the neurovascular bundle and urethra. Other embodiments also envision using MRI or CT scan guidance methods as they become available in the future. Another embodiment could also use transurethral injection of the trichothecenes using devices and methods similar to TUNA, except substituting the heating needles with injecting needles.

It should be noted that in addition to the benefits of apoptotic chemosurgery over mechanical necrotic surgery previously discussed, the treatment option for BPH using TRUS as described above also has several additional advantages over TUNA or TUMT. Since both TUNA and TUMT only ablate prostate tissue around the urethra, their therapeutic benefit is less likely to last as long as the 50% total prostate ablation method presented above. Furthermore, ablation of a significant amount of the prostate should have a corresponding reduction in the risk for prostate cancer. Autopsies of men in their 80's have shown >90% show hyperplastic changes and >70% malignant changes in the prostate gland (per Harrison's Principles of Internal Medicine, 15th edition, McGraw Hill, 2000, page 608). Since cancer starts with a singe aberrant cell, significantly reducing the absolute number of cells, particularly in an already enlarged prostate, would mathematically be expected to at least proportionately reduce the subsequent risk for prostate cancer.

EXAMPLE 1B

Same as example 1A except that the prostate is enlarged to 125 grams or ~5 times its normal size. The decision is made to use a maximum "ultra safe" dose to achieve maximum possible ablation of the prostate in one administration. A 5,500 ng amount of satratoxin is mixed with propylene glycol and administered by a plurality of hypodermic injections into the prostate, facilitated by the use of a transrectal ultrasound imaging device (TRUS) with template guidance. Likewise, if a maximum "safe" dose level is chosen, a 27,500 ng dose of satratoxin would be mixed with a suitable carrier and administered as above. Administration is made into selected areas of the prostate, substantially far enough away from the urethra to avoid damaging it.

This example illustrates another acceptable method of dosaging. It also illustrates that ablation need not be symmetrical (i.e. uniformly distributed)—as an example almost all of the prostate may be ablated except the portion around the urethra.

EXAMPLE 2

A patient presents with an excessive amount to adipose tissue below their chin and would like it removed for cosmetic reasons. An 80% ablative dose is chosen. The dose of trichothecene is mixed in ethanol and placed in a hypodermic needle. The hypodermic needle is inserted almost all of the way through the adipose mass, then the plunger is depressed continually as the hypodermic needle is retracted, resulting in a substantially columnar administration pattern along the retraction track and through the adipose mass. This is repeated several times at fairly uniform spacing along the adipose mass to achieve approximately homogenous distribution of therapeutic in the mass of fat cells.

Other Embodiments

It should be understood that the doses presented above are guidelines only and the concentrations presented in this application should not be construed as "optimal". As is customary under prior art, all dosages would be further refined and scrutinized by in vivo testing in suitable animal models and in Phase I and II clinical trials on humans as required by the FDA and the lowest concentrations suitable to achieve a desired amount of ablation would likely be called "optimal". The doses presented in this application were done so to fulfill the reduction to practice requirement of this application and are not intended to imply an absolute standard or "optimal" dose but are merely some representative examples of efficacious, yet safe, embodiments of present invention.

Present invention also envisions directly incorporating any other substances into pharmaceutical compositions of present invention that may facilitate application, enhance delivery or uniformity of distribution, or in any way increase efficacy of therapeutics of present invention, including adding substances that function by alternative mechanisms of action or complementary mechanisms of action. As an example, combinations of different trichothecenes with varying rates of internalization may be used to enhance more homogenous distribution within a tissue mass rather than using a single trichothecene. Also, therapeutics of present invention may be administered in any suitable carrier in place of the ethanol or propylene glycol presented in the examples. Adjuvant therapies may also be used in conjunction with present invention, either as part of pharmaceutical compositions of present invention or administered separately into the blood stream. An example of an adjuvant therapy could include drugs to enhance blood clotting or boost red cell counts (e.g. antihemorrhagics, plasma derived and synthetic coagulation factors, autologous transfusions, etc . . . ) to minimize any small blood vessel bleeding caused by either the hypodermic needles or potential subsequent ablation of small blood vessels by therapeutics of present invention.

Nothing in the application is intended to limit the devices and methods used to facilitate administration of either therapeutics or pharmaceutical compositions of present invention. Other devices, either currently existing, or to be developed in the future that are capable of interstitial administration could also be employed.

Examples of dosaging are not absolute. As an example, if one desires to ablate 100% of a nucleated tissue mass, they are not limited to using the 100% ablative dose as described but can use much larger doses, up to the "safe" level defined within this application, or up to any other level defined, or demonstrated, to be reasonably "safe". A dose chosen in such a manner may well be several times the required dose and yet be systemically "safe". Present invention also envisions the possibility achieving a desired amount of ablation over several administration cycles.

The tissues targeted for ablation are only a few of the innumerable possibilities intended by present invention. As an example, apoptotic chemosurgery may be employed to either partially or completely ablate tissue including but not limited to, ablation of infected or diseased portions of the liver, partial ablation of a hyperactive thyroid, complete ablation of a seizure producing area of brain tissue, complete ablation a tissue mass un undergoing autoimmune attack, etc . . . The ablation area may also be extended to include a perimeter outside the area targeted for ablation to provide a safety margin.

The methods provided may also be used in conjunction with conventional surgery or endoscopic, laparoscopic, or aspirating techniques wherein a portion of an organs is completely ablated and the dead tissue or any remaining connective tissue is removed with existing surgical of aspirating methods some time later. Nothing in present invention is intended to limit ablation of tissue to procedures involving ablation of nucleated cells. As an example, if a non nucleated tissue mass or lesion is chosen for removal, the area of nucleated cells around the lesion may be ablated leaving the non nucleated tissue mass detached, thus facilitating subsequent removal by aspiration or surgical means.

The scope and intent of the present invention is to provide novel compositions and methods which will constitute the next generation of organ or tissue ablation procedures.

I claim:

1. A method of chemical surgery for non malignant cell populations in humans or non-human animals, comprising interstitial administration of locally toxic amounts of trichothecene or trichothecenes, directly into a tissue mass targeted for ablation in said humans or animals, whereby a means of obviating surgery or other necrosis inducing ablation procedures will be provided.

2. The method of claim 1 wherein said interstitial administration is by hypodermic needle, said hypodermic needle being inserted to a given point and the contents of said hypodermic needle being injected as said hypodermic needle is being retracted, whereby a substantially columnar perfusion of trichothecene or trichothecenes will be administered into said tissue mass targeted for ablation.

3. The method of claim 2 wherein said interstitial administration by said hypodermic needle is repeated more than once and in different locations, whereby a plurality of substantially columnar perfusions of trichothecene or trichothecenes will be administered into said tissue mass targeted for ablation.

4. The method of claim 1 wherein said interstitial administration is by TRUS guidance or other means of delivering or facilitating the delivery of trichothecene or trichothecenes interstitially into a tissue mass.

5. The method of claim 1 wherein said locally toxic amount of trichothecene or trichothecenes is an amount adequate to inhibit approximately 100% of protein synthesis activity in a sub population of cells within said tissue mass targeted for ablation.

6. The method of claim 1 wherein said trichothecene is a fragment or sub-unit of trichothecene which still possess the biological activity of inhibiting protein synthesis.

7. The method of claim 1 wherein said tissue mass targeted for ablation is adipose tissue.

8. The method of claim 1 wherein said tissue mass targeted for ablation is an enlarged prostate.

9. The method of claim 1 wherein said trichothecene is a molecule that contains a sesquiterpene epoxide structure and is capable of inhibiting protein synthesis.

* * * * *